United States Patent [19]
Seneker et al.

[11] Patent Number: 5,455,374
[45] Date of Patent: Oct. 3, 1995

[54] LIQUIFICATION OF TRANS, TRANS-4,4'-DIISOCYANATE DICYCLOHEXYLMETHANE BY PARTIALLY REACTING THE ISOCYANATE GROUPS WITH BLOCKING AGENTS

[75] Inventors: Stephen D. Seneker, Paden City; Scott A. Kane, New Martinsville, both of W. Va.

[73] Assignee: Bayer Corporation, Pittsburgh, Pa.

[21] Appl. No.: 85,234

[22] Filed: Jun. 30, 1993

[51] Int. Cl.$^6$ .................................................. C07C 249/00
[52] U.S. Cl. .......................... 560/330; 560/331; 560/351
[58] Field of Search .................. 560/339, 351, 560/330, 331

[56] References Cited

U.S. PATENT DOCUMENTS 4,363,686  12/1991  Komarek ........................... 156/242
5,071,937  12/1991  Potter et al. ....................... 528/45
5,175,350  12/1992  Seneker et al. .................... 560/352
5,232,988  8/1993  Venham et al. .................... 525/124
5,280,100  1/1994  Venham ............................ 528/45

Primary Examiner—José G. Dees
Assistant Examiner—Samuel Barts
Attorney, Agent, or Firm—Joseph C. Gil; N. Denise Brown

[57] ABSTRACT

The present invention relates to a liquid, storage-stable isocyanate having a viscosity of less than 100,000 mPa.s at 23° C. and an isocyanate content of from about 9 to 20% by weight, and is prepared by reacting a solid 4,4'-methylene bis(cyclohexyl isocyanate) with a blocking agent. The 4,4'-methylene bis(cyclohexyl isocyanate) must contain at least 35 to 100% by weight of the trans,trans isomer. More generally, this liquid isocyanate is prepared by reacting the solid or semi-solid 4,4'-methylene bis (cyclohexyl isocyanate) with the blocking agent in quantities such that at least 22% but less than 60% of the isocyanate groups are blocked. Preferred blocking agents are the ketoximes, and mixtures thereof.

7 Claims, No Drawings

LIQUIFICATION OF TRANS, TRANS-4,4'-DIISOCYANATE DICYCLOHEXYLMETHANE BY PARTIALLY REACTING THE ISOCYANATE GROUPS WITH BLOCKING AGENTS

BACKGROUND OF THE INVENTION

This invention relates to liquid, storage-stable isocyanates prepared by reacting 4,4'-methylene bis(cyclohexyl-isocyanate) having a trans,trans-isomer content of from 35 to 100% by weight with a blocking agent.

4,4'-diisocyanato dicyclohexylmethane and the diamine precursor, 4,4'-diamino-dicyclohexylmethane, exist in three stereoisomeric forms (i.e. trans,trans; cis,trans; and cis,cis) as described, for example, in U.S. Pat. Nos. 2,606,925 and 3,789,032, Canadian Patents 961,049 and 971,184, and British Patent 1,220,715. Commercial grades of 4,4'-diamino-dicyclohexylmethane normally contain all three isomers.

U.S. Pat. No. 3,155,724 describes a process of producing 4,4'-diisocyanato dicyclohexylmethane from the amine precursor, wherein the resultant product has a trans,trans-isomer content of 54% and a melting point of about 58° C. Accordingly, the 4,4'-diisocyanate dicyclohexylmethane is a semi-solid or slurry at room temperature.

In order for mixtures containing 4,4'-diisocyanato dicyclohexylmethane to be a liquid at room temperature, the content of the trans,trans-isomer must lie within a certain range. Liquid diisocyanate mixtures can be prepared by the phosgenation of 4,4'-diamino-dicyclohexylmethane (4,4'-HMDA), or its mixtures with the 2,4'- and/or 2,2'-HMDA isomers, wherein the content of the trans,trans-isomer of 4,4'-HMDA is less than about 25%. The trans,trans-isomer content of the diisocyanate corresponds to that of the amine precursor.

U.S. Pat. No. 5,175,350 discloses a process for the preparation of a 4,4'-diisocyanato dicyclohexylmethane which contains at least 90% by weight of the trans,trans-isomer. The process yields a liquid phase which contains from about 12 to about 25% by weight of the trans,trans-isomer, and a solid phase which contains at least about 90% by weight of the trans,trans-isomer.

U.S. Ser. No. 07/772,996, filed Oct. 8, 1991, describes a process for preparing free-flowing solids, which have many or the advantages of liquids, from 4,4'-diisocyanato dicyclohexylmethane having a trans,trans-isomer content of at least 90% by weight.

There are obvious advantages to a liquid diisocyanate compared to those that are fused solids or slurries at ambient temperature. A liquid is easier to pump and less expensive to transport. A liquid has a homogeneous composition as supplied without the need to homogenize it at elevated temperatures as is the case with slurries or fused solids. In the production of polyurethanes, a liquid can be added easily by weight or volume and combined with suitable coreactants at ambient temperatures. This is safer than using the materials at elevated temperatures due to the lower vapor pressure of the materials at room temperature.

DESCRIPTION OF THE INVENTION

The present invention is directed to a liquid, storage-stable isocyanate prepared by reacting 4,4'-methylene bis-(cyclohexyl isocyanate) having a trans,trans isomer content of from 35 to 100% by weight, preferably of from 45 to 97% by weight, and most preferably of from 80 to 95% by weight, with a blocking agent. The prepared liquid isocyanates have an isocyanate group content of from 9 to 20% by weight, preferably from 10 to 18% by weight, and most preferably from 11 to 15% by weight, and viscosities of less than 100,000 mPa.s at 23° C. Generally, these isocyanates can be prepared by reacting 4,4'-methylene bis(cyclohexyl isocyanate) with the blocking agent in quantities such that at least 22%, but less than 60% of the isocyanate groups, react with the blocking agent. It is preferred that from about 33 to 55% of the isocyanate groups react with the blocking agent. Most preferably, about 39 to 50% of the isocyanate groups react with the blocking agent.

As used herein, the term "liquid" is defined as "a solution having a viscosity below 100,000 mPa.s at 23° C. with no crystals visible to the unaided eye". The term "storage-stable" means "a clear liquid after 3 weeks at room temperature with no crystals visible to the unaided eye".

A blocking agent is a compound which combines reversibly with 4,4'-methylene bis(cyclohexyl isocyanate) to form a thermally labile adduct that dissociates at temperatures below 180° C. The amount of blocking agent to be used is such that at least 22% but less than 60% of the isocyanate groups react with the blocking agent. If less than 22% of the NCO groups are blocked, the solutions do not remain as liquids. Also, viscosity increases significantly as the percent of blocked isocyanate groups increases. The range of at least 22% to less than 60% of blocked isocyanate groups results in a balance between liquidity and viscosity of the prepared isocyanates.

4,4'-methylene bis(cyclohexyl isocyanate) of the desired trans,trans-isomer content can be prepared by various methods as disclosed in the prior art. For example, the hydrogenation of bis-(4-aminophenyl)-methane yields the corresponding cyclohexyl compound, which may contain up to about 50% by weight of the trans,trans-isomer. The hydrogenated amine mixture can be subjected to a crystallization process to obtain an amine mixture having a higher trans, trans-isomer content, i.e. up to about 80% by weight. Suitable processes are disclosed in U.S. Pat. Nos. 2,494,563, 3,153,088, 3,384,661, and 3,393,236. Blending of amine mixtures having different trans,trans-isomer contents can be used to produce other trans,trans-isomer contents. Phosgenation of the amine mixtures produces the corresponding mixture of diisocyanates containing the same amount of trans,trans-isomer as the amine mixtures. 4,4'-diisocyanato dicyclohexylmethane with high trans,trans-isomer contents can also be obtained through the crystallization of diisocyanate isomer mixtures. Suitable processes are disclosed in U.S. Pat. Nos. 4,983,763 and 5,175,350, incorporated herein by reference.

Suitable blocking agents which can be used to liquify the trans,trans-4,4'-diisocyanato dicyclohexylmethane in accordance with the present invention are known blocking agents for polyisocyanates. Examples of these blocking agents include monophenols such as phenol, nonylphenol, the cresols, the trimethyl phenols and the tert butyl phenols; compounds which easily form enols such as acetoacetic ester, acetyl acetone and malonic acid derivatives, e.g., malonic acid diethylester; lactams such as ε-caprolactam and ε-valerolactam; oximes such as acetone oxime, butanone oxime, methylamyl ketoximes and cyclohexanone oxime; and triazoles such as 1H-1,2,4-triazole. Mixtures of blocking agents may also be used.

Preferred blocking agents are ketoximes such as methylethyl ketoxime and methylamyl ketoxime. It is particularly preferred to use mixtures of ketoximes as blocking agents. Such as, for example, equimolar amounts of methylethyl ketoxime and methylamyl ketoxime.

The 4,4'-diisocyanato dicyclohexylmethane is typically charged to the reaction vessel as a melted homogeneous mixture. The temperature of the melted mixture can vary from 50° to 90° C. depending on the trans,trans-isomer content of the isocyanate. The higher the trans,trans-isomer content, the higher the melt temperature. The reaction vessel is maintained at a temperature which keeps the isocyanate as a homogeneous liquid.

The blocking agent can be added as a liquid or solid. The reaction temperature is normally maintained below 150° C., and preferably between about 50° and 130° C. The reaction is continued until the isocyanate content of the reaction mixture decreases to the theoretical amount or slightly below that amount. The reaction product can have an isocyanate content of about 9 to 20% by weight, preferably about 10 to 18% by weight, and most preferably about 11 to 15% by weight. The reaction product is a liquid, storage-stable isocyanate having a viscosity of less than 100,000 mPa.s at 23° C. and does not form crystals after 3 weeks at room temperature.

The liquid, storage-stable isocyanates can be used for the preparation of polyurethanes or polyureas and, in particular, polyurethane or polyurea coatings, adhesives, sealants, patching compounds, and elastomers. These polyurethanes are prepared by the reaction of the isocyanates with glycols and/or polyols, and chain extenders and/or crosslinkers. Polyureas are prepared by the reaction of the isocyanates with diamines and/or polyamines, and chain extenders and/or crosslinkers.

The invention is further illustrated, but is not intended to be limited by the following examples in which all parts and percentages are by weight unless otherwise specified.

EXAMPLES

Examples 4 and 5 are comparative examples and were conducted to determine the limits of the invention.

Example 1

A 250 ml flask was charged with 4,4'-methylene bis(cyclohexyl isocyanate) (49.8% trans,trans-isomer) (131.2 g: 1.000 eq.). The diisocyanate was heated to 60° C. Methylamyl ketone (MAKO) (51.6 g: 0.400 eq.) was added over a 10 minute period, during which time the temperature of the reaction mixture rose to 93° C. The mixture was stirred while the temperature was held at 90° C. for an additional 45 minutes. A 100 g sample of the product (theoretical NCO= 13.8%) was poured into a 4 oz. jar and stored at room temperature. After 3 weeks, the viscosity at 23° C. was 3200 mPa.s and the solution had remained clear with no evidence of crystal formation.

Example 2

A 250 ml flask was charged with 4,4'-methylene bis(cyclohexyl isocyanate) (49.8% trans,trans-isomer) (131.2 g: 1.000 eq.).

The diisocyanate was heated to 65° C. ε-caprolactam (45.28 g: 0.400 eq.) was added over a 5 minute period. After the addition, the mixture was heated to 70° C., and the heat source removed. The reaction exotherm raised the temperature of the solution to 120° C. The mixture was allowed to cool to 90° C. and held there for 45 minutes. A 100 g sample of the product (theoretical NCO=14.3%) was poured into a 4 oz. jar and stored at room temperature. After 3 weeks, the viscosity at 24° C. was 52,000 mPa.s, and the solution had remained clear with no evidence of crystal formation.

Example 3

A 250 ml flask was charged with 4,4'-methylene bis(cyclohexyl isocyanate) (49.8% trans,trans-isomer) (131.2 g: 1.000 eq.). The diisocyanate was heated to 80° C. Ethylacetoacetate (52.08 g: 0.400 eq.) was added slowly through a dropping funnel to the hot diisocyanate. No exotherm was observed upon addition of the blocking agent. The mixture was heated to 100° C. for 3.0 hours, then the temperature was increased to 110° C. and held for 5.0 hours. The reaction mixture was stored at 95° C. overnight, and heated the following day to 100° C. for an additional 3.0 hours. Following this final heating, the NCO content was found to be 13.89% (theoretical NCO=13.75%). After storage for 3 weeks at room temperature, the viscosity of the clear-brown liquid was 2300 mPa.s, and the NCO content was 13.79%. Storage for 2 months at room temperature did not lead to crystallization.

Example 4 (Comparative Example)

A 1000 ml 3-necked flask was charged with 4,4'-methylene bis(cyclohexyl isocyanate) (49.8% trans,trans-isomer)(600 g: 4.573 eq.) and heated to 70° C. A mixture of methylethyl ketoxime (MEKO) (39.78 g: 0.457 eq.) and methylamyl ketoxime (MAKO) (58.99 g: 0.457 eq.) was added through an addition funnel over a 15 minute period. The temperature of the reaction mixture was held at 90° C. for 45 minutes after the addition was completed. The reaction mixture was allowed to cool to room temperature, and a 100 g sample was withdrawn and stored at room temperature (theoretical NCO=22.0%). The viscosity at 24° C. was determined to be 276 mPa.s. After 18 days at room temperature, the sample began to crystallize. The remainder of the reaction product (20% blocked NCO) was used to produce more highly blocked 4,4'-methylene bis(cyclohexyl isocyanate) as described in Example 6.

Example 5 (Comparative Example)

A 1000 ml round bottomed flask was charged with 4,4'-methylene bis(cyclohexyl isocyanate) (97% trans,transisomer) (300.0 g: 2.286 eq.). The diisocyanate was heated to 90° C., and a mixture of MEKO (59.70 g: 0.686 eq.) and MAKO (88.5 g: 0.686 eq.) was added over a 10 minute period. The temperature of the reaction mixture was held at 90° C. for 30 minutes. A 100 g sample (theoretical NCO= 8.6%) was withdrawn and stored at room temperature. After 3 weeks at room temperature, the viscosity of the solution was 350,000 mPa.s (23.0° C.), and there was no evidence of crystallization.

Example 6

A round-bottomed flask was charged with the MEKO/ MAKO blocked 4,4'-methylene bis(cyclohexyl isocyanate) described in Example 4 above (598.77 g: 3.135 eq.). The diisocyanate was heated to 90° C. before adding a mixture of MEKO (8.53 g: 0.098 eq.) and MAKO (12.64 g: 0.098 eq.) through an addition funnel. The reaction mixture was kept at 90° C. for 30 minutes after the addition of the blocking agents. A 100 g sample of the product (theoretical NCO=19.9%) was stored at room temperature. After 3 weeks at room temperature, the viscosity was 574 mPa.s and there was no evidence of crystallization.

Example 7

A round bottomed flask was charged with 4,4'-methylene bis(cyclohexyl isocyanate) (97% trans,trans-isomer) (334.0 g: 2.546 eq.). The diisocyanate was heated to 90° C. and a mixture of MEKO (44.30 g: 0.509 eq.) and MAKO (65.68 g: 0.509 eq.) was added over a fifteen minute period. The temperature of the reaction mixture was held at 90° C. for 30 minutes. A 100 g sample (theoretical NCO=14.4%) was withdrawn and stored at room temperature. After 3 weeks at room temperature, the viscosity of the solution was 6600 mPa.s (23.0° C.), and there was no evidence of crystallization.

Example 8

A round bottomed flask was charged with 4,4'-methylene bis(cyclohexyl isocyanate) (80% trans,trans-isomer) (370.6 g: 2.825 eq.). The diisocyanate was heated to 90° C. and a mixture of MEKO (67.54 g: 0.777 eq.) and MAKO (100.21 g: 0.777 eq.) was added slowly to the reaction mixture. The temperature was maintained at 90° C. for 30 minutes, before allowing the mixture to cool to room temperature. After three weeks at room temperature, the product (theoretical NCO=9.7%) had a viscosity of 99,000 mPa.s at 23° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A liquid, storage-stable isocyanate having a viscosity of less than 100,000 mPa.s at 23° C. and an isocyanate group content of from about 9 to 20% by weight, prepared by reacting
   a) a solid or semi-solid mixture of 4,4'-methylene bis(cyclohexyl isocyanate) stereoisomers containing from 35 to 100% by weight of the trans,trans-isomer, and
   b) a blocking agent, or a mixture of two or more blocking agents.

2. The liquid, storage-stable isocyanate of claim 1, wherein said isocyanate group content is from about 10 to 18% by weight.

3. The liquid, storage-stable isocyanate of claim 1, wherein said isocyanate group content is from about 11 to 15% by weight.

4. The liquid, storage-stable isocyanate of claim 1, wherein said blocking agent is a ketoxime.

5. The liquid, storage-stable isocyanate of claim 1, wherein said blocking agent is a mixture of two or more ketoximes.

6. The liquid, storage-stable isocyanate of claim 5, wherein said mixture comprises methylethyl ketoxime and methylamyl ketoxime.

7. The liquid, storage-stable isocyanate of claim 6, wherein said methylethyl ketoxime and said methylamyl ketoxime are present in equimolar quantities.

* * * * *